United States Patent [19]
Caizza

[11] Patent Number: 6,086,568
[45] Date of Patent: Jul. 11, 2000

[54] SYRINGE PLUNGER ROD FOR RETRACTING NEEDLE SYRINGE

[75] Inventor: Richard Caizza, Barry Lakes, N.J.

[73] Assignee: Becton Dickinson and Company, Franklin Lakes, N.J.

[21] Appl. No.: 09/419,183

[22] Filed: Oct. 15, 1999

[51] Int. Cl.⁷ .................................................. A61M 5/00
[52] U.S. Cl. ..................... 604/218; 604/220; 604/110; 604/195
[58] Field of Search ..................... 604/218, 220, 604/187, 110, 195, 198, 263, 221

[56] References Cited

U.S. PATENT DOCUMENTS

| | | | |
|---|---|---|---|
| 5,263,934 | 11/1993 | Haak | 604/110 |
| 5,700,247 | 12/1997 | Grimard et al. | 604/220 |
| 5,762,635 | 6/1998 | Pace et al. | 604/218 X |
| 5,814,017 | 9/1998 | Kashmer | 604/220 X |

*Primary Examiner*—John D. Yasko
*Attorney, Agent, or Firm*—Keith J. McWha; John L. Voellmickle

[57] ABSTRACT

An improved syringe plunger rod for a retracting needle syringe is illustrated having a plunger rod with inner and outer members and a retaining ring. The retaining ring restricts movement between the inner and outer members until the ring makes contact with the proximal end of the retracting needle syringe and further distal force is applied to the inner member. Once disengaged, the inner member moves relative to the outer member to activate the retractable needle syringe. One advantage of the improved plunger rod is that it reduces the probability of premature activation of the retractable needle syringe. In addition, the improved plunger rod assists in the prevention of re-use of the syringe.

20 Claims, 9 Drawing Sheets

SYRINGE PLUNGER ROD FOR RETRACTING NEEDLE SYRINGE

FIELD OF THE INVENTION

This invention relates to a medical syringe device and, more particularly to a non-reusable, retractable needle syringe having an improved syringe plunger which prevents the pre-activation of the retracting needle.

BACKGROUND OF THE INVENTION

In the medical arts, sharp pointed needles are used for a variety of procedures. Devices having sharp pointed needles are used for example, in administering fluids to patients either directly or in through intravenous apparatus. In addition, needles are used in various blood drawing applications either with syringes or specialized holders for filing collection tubes.

The medical profession recognizes exposure to blood borne pathogens as a potential hazard. As a result of this recognition, numerous protocols for use of needles have been developed and are widely practiced. The problem of transmission of blood borne pathogens not only exists for the physician, nurse or phlebotomist using the needles but also for the support staff throughout the hospital. Since most needles in use today are single-use and disposable, hospital service personnel like housekeeping, laundry and maintenance are at risk from needles that are not properly handled by the users.

The use protocols generally dictate in detail when and how a needle is used and how it should be disposed. The problem with many protocols for handling needles is that the protocols often require users to perform additional steps in the procedure. Certain practices regarding handling of used needles are sometimes disregarded and injuries still occur. The medical device industry has responded to the problem by producing a wide variety of needle shielding devices and retractable needle syringes to assist practitioners in their need to reduce the occurrence of needle injuries.

There has been increased emphasis in designing hypodermic syringes with extendible shields which protect and project over the needle area after injections are completed. Although these devices are well suited to reduce the occurrence of needle injuries, some such devices can be cumbersome and difficult to dispose.

A growing area in the medical device industry to limit the exposure of blood borne pathogens is in the area of retractable needle syringes. Retractable needle syringes generally allow the needle to retract within the syringe after the syringe has been used. The syringe usually includes a hollow plunger which is inserted into one end of the syringe barrel. The syringe usually includes a spring or some other resilient means to push the used needle into the hollow plunger rod. Other retractable needle syringes use a means to pull the used syringe and hub into the syringe barrel where the plunger rod is then broken off to discourage re-use of the syringe. In both of these configurations of retractable needle syringes, the plunger rod usually activates the mechanism to retract the needle or the needle hub. These designs allow retraction of the needle while the plunger rod is forced in the same direction as the injection. The purpose of that design function is reportedly to allow the user a one-handed technique to retract the needle in the syringe thereby avoiding exposure to the sharp end of the needle.

However, these designs have a tendency to prematurely activate as the user is injecting the medication with the syringe. Also, these devices can prematurely activate during manufacture of the syringes when the plunger rod is inserted into the back end of the syringe barrel.

There remains a need for an improved design of a syringe in which the plunger rod does not prematurely activate the retracting means to retract the needle within the syringe. There is also a need to prevent reuse of the syringe and allow safe and easy disposal.

SUMMARY OF THE INVENTION

The present invention provides an improved syringe plunger rod for a retractable needle syringe. The retractable needle syringe includes a barrel having a proximal end and a distal end. A plunger assembly is disposed in the barrel. The assembly has an inner member, an outer member and a retaining ring. The inner member is removably engaged in the outer member. The retaining ring is disposed on the outer member to restrict movement between the inner and outer members until the retaining ring comes into contact with the proximal end of the syringe barrel. The inner member is forced distally to disengage the inner member from the outer member which allows movement of the inner member within the outer member and activation of the retractable needle syringe.

The inner member further includes at least one first detent and the outer member includes at least one second detent for removably fitting into the first detent. A shoulder portion adjacent to the second detent is included on the outer member for supporting the retaining ring.

DETAILED DESCRIPTION

Figure 1:
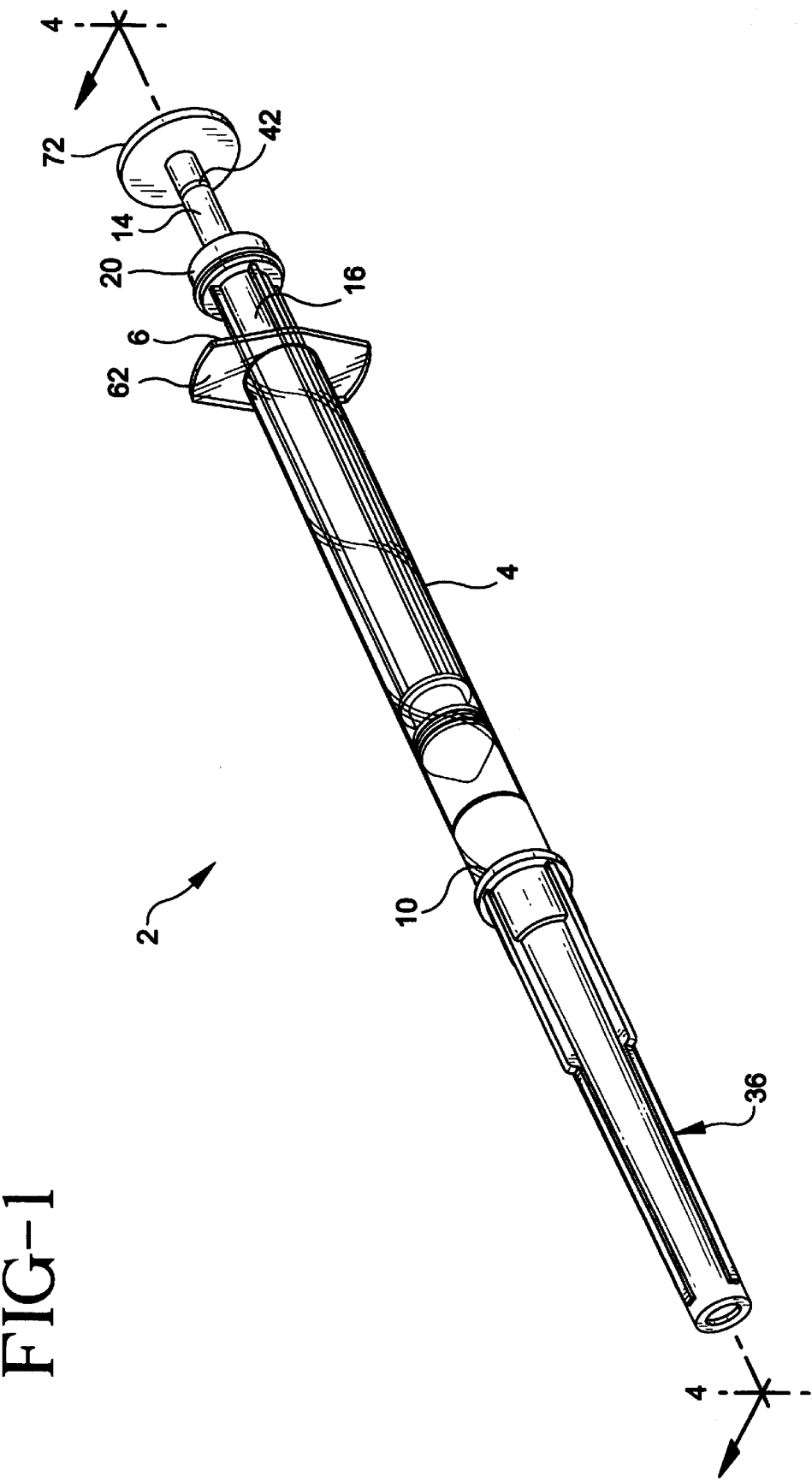
FIG. 1 is a perspective view of the present invention assembled to a retractable needle syringe.
Figure 2:
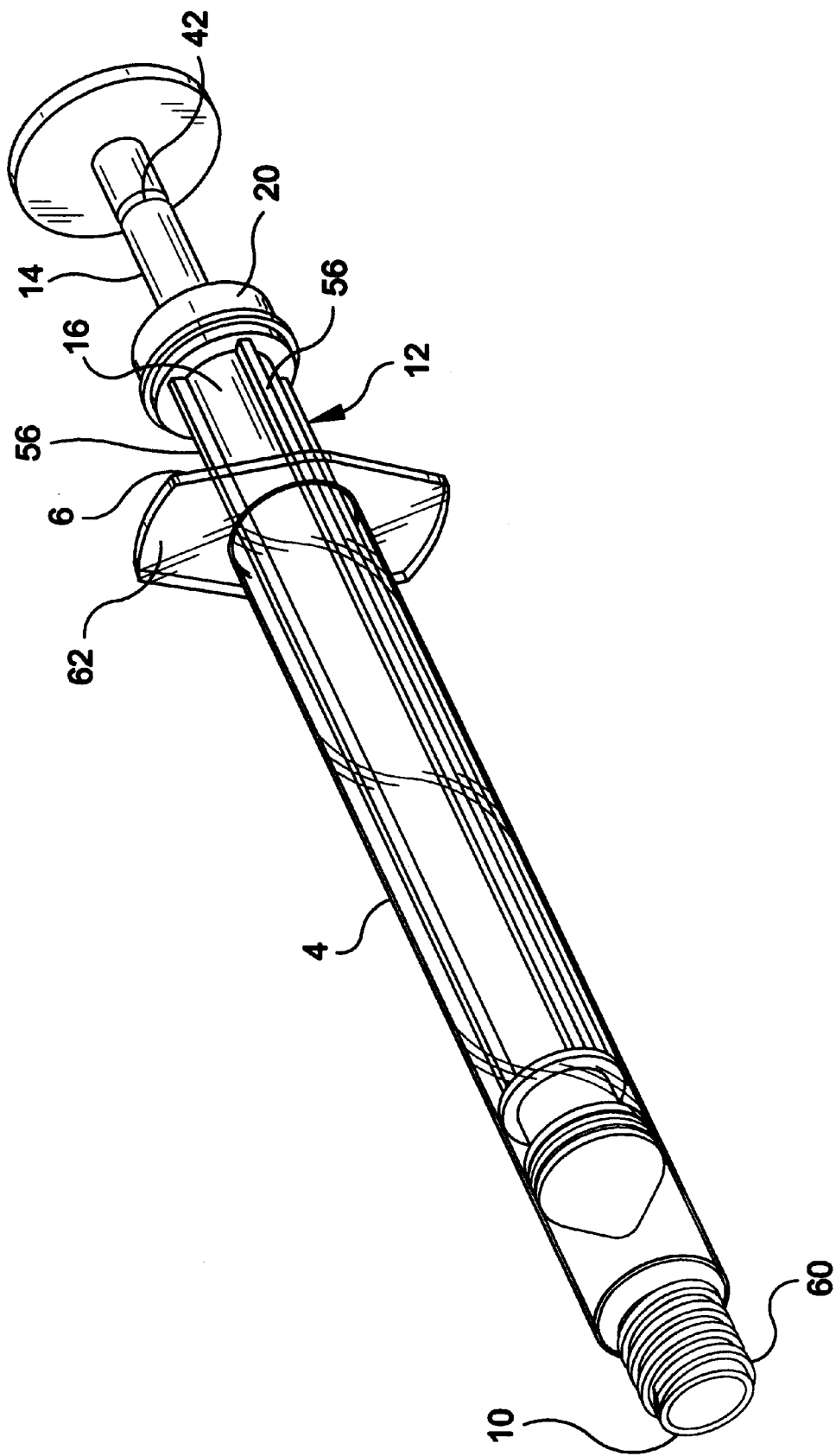
FIG. 2 is a perspective view of FIG. 1 without the needle assembly attached.

While this invention is satisfied by embodiments in many different forms, there is shown in the drawings and herein described in detail preferred embodiments of the invention with the understanding that the present disclosure is to be considered exemplary of the principles of the invention. It is not intended to limit the scope of the invention to these embodiments illustrated. The scope of the invention is measured by the appended claims and their equivalents.

Adverting to the drawings, FIGS. 1–9 illustrate the present invention of an improved syringe plunger rod assembly 12 for a retracting needle syringe 2. Assembly 12 includes an inner member 14, an outer member 16, and a retaining ring 20. Plunger assembly 12 is disposed inside a barrel 4 as shown in FIG. 1. Without the retaining ring, the inner member can freely slide within the outer member when sufficient force is applied to the inner member.

Figure 6:
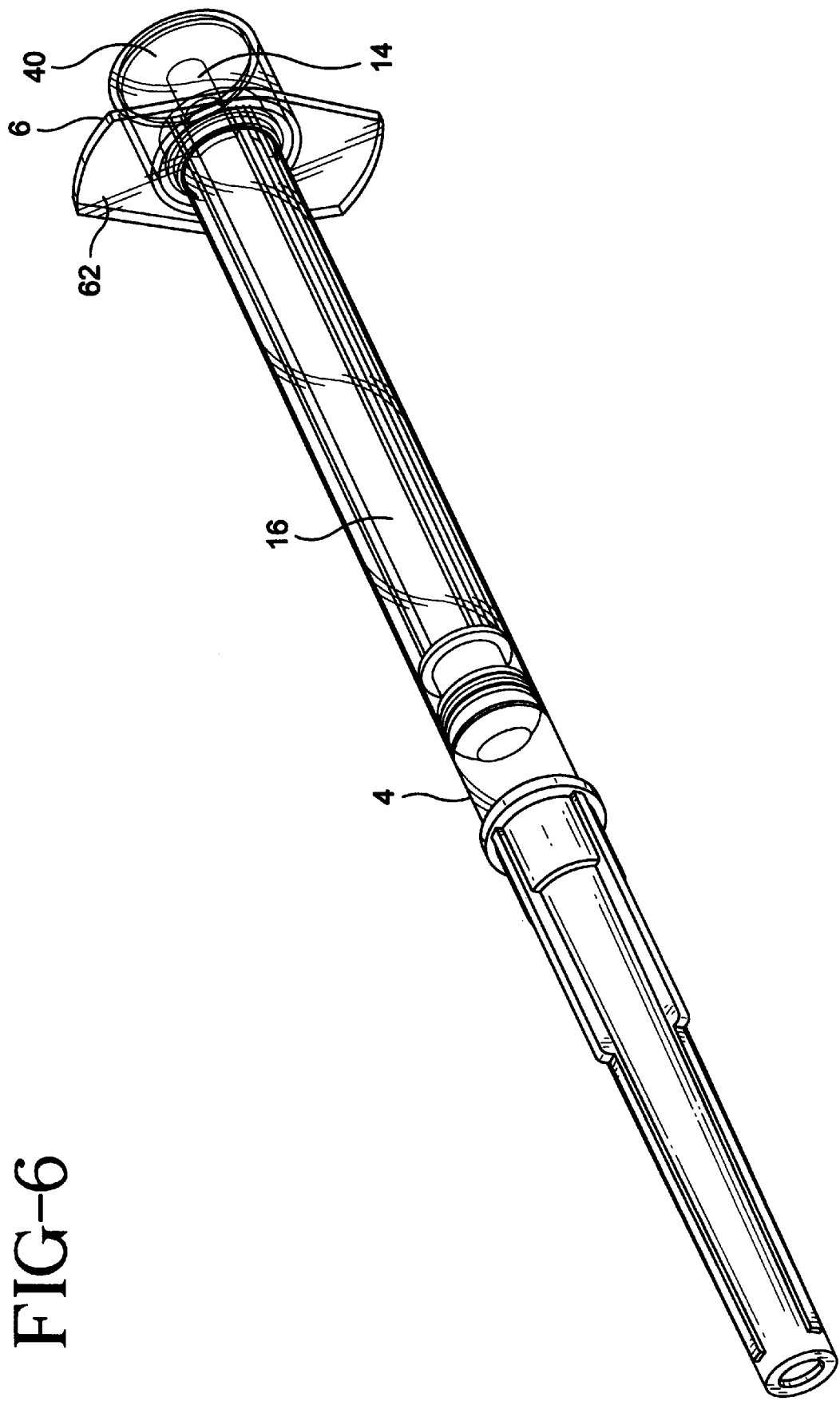
FIG. 6 is a perspective view of FIG. 1 with an annular sleeve and the plunger rod assembly fully depressed with the retractable needle syringe activated.

Barrel 4 has a proximal end 6 and a distal end 10. At the distal end, barrel 4 preferably has an external thread 60 for attachment to a needle assembly 36. However, other attachment structures could be provided, such as a luer lock, a luer slip, or a removable snap fit. Thus, plunger assembly 12 can be used with any retractable needle syringe that has the needle assembly attached to the distal end of the barrel and requires actuation from the plunger rod. Barrel 4 also includes a flange 62 at the proximal end to assist the user in expelling fluid out of the syringe. In an alternate embodiment, the barrel includes an annular sleeve 40 attached to the proximal end of the barrel as seen in FIG. 6. Sleeve 40 is used in this embodiment to discourage users from re-using the syringe by burying the plunger within the annular sleeve so that the plunger assembly can not be withdrawn after it is fully depressed.

Figure 3:
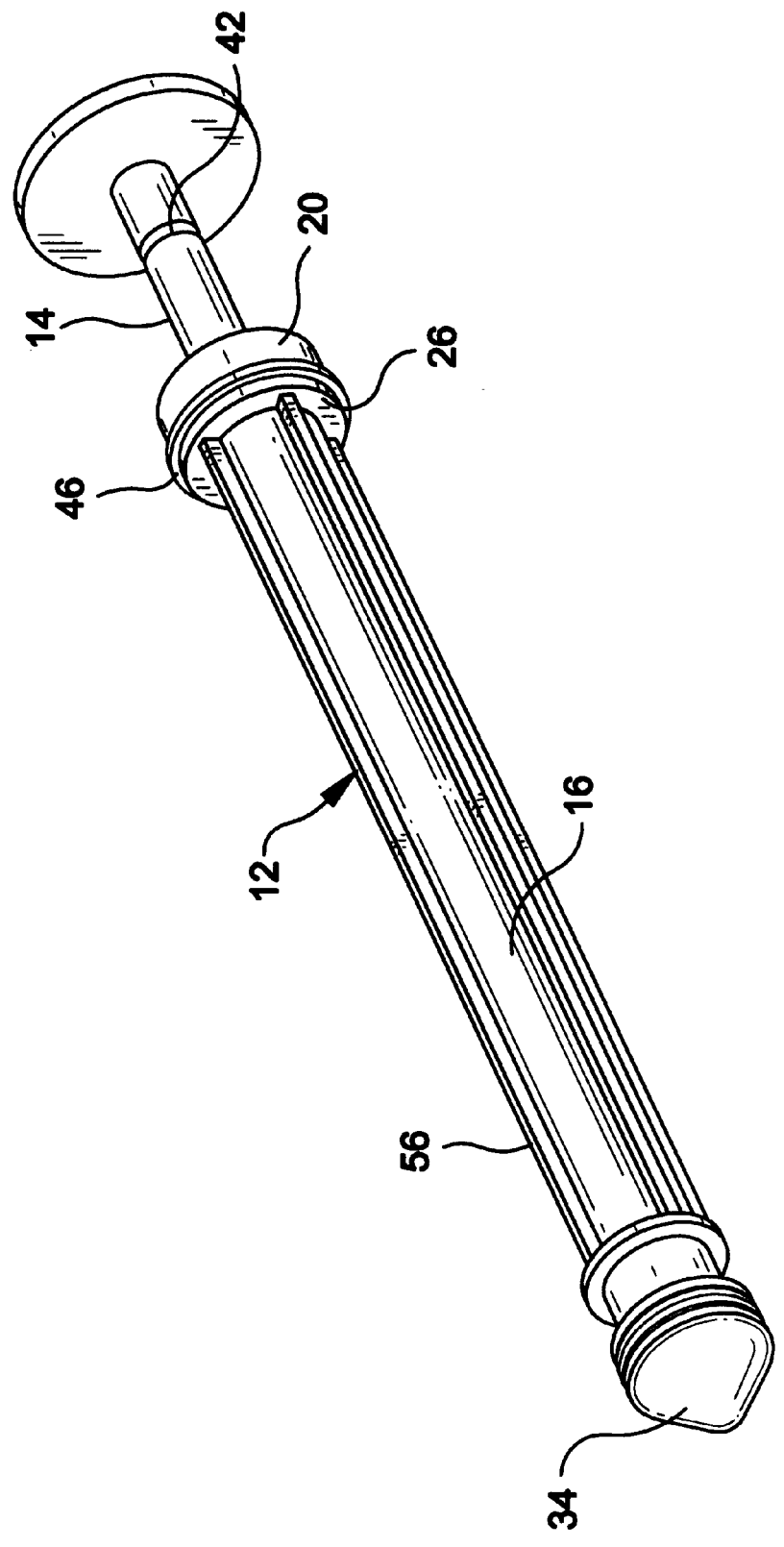
FIG. 3 is a perspective view of an improved syringe plunger rod assembly.
Figure 7:
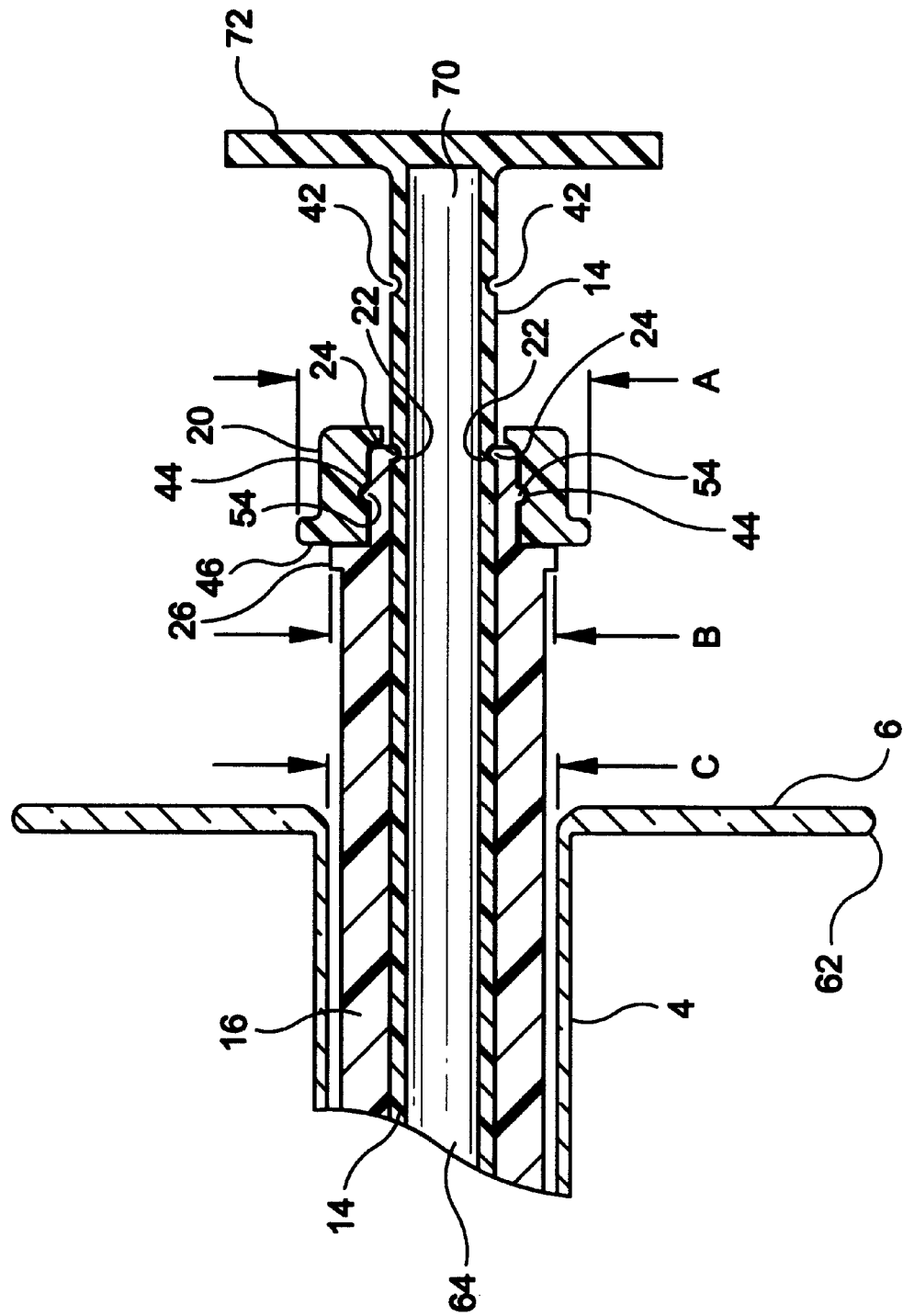
FIG. 7 is an enlarged view of FIG. 4 with the plunger rod assembly extended and retractable syringe inactivated.
Figure 8:
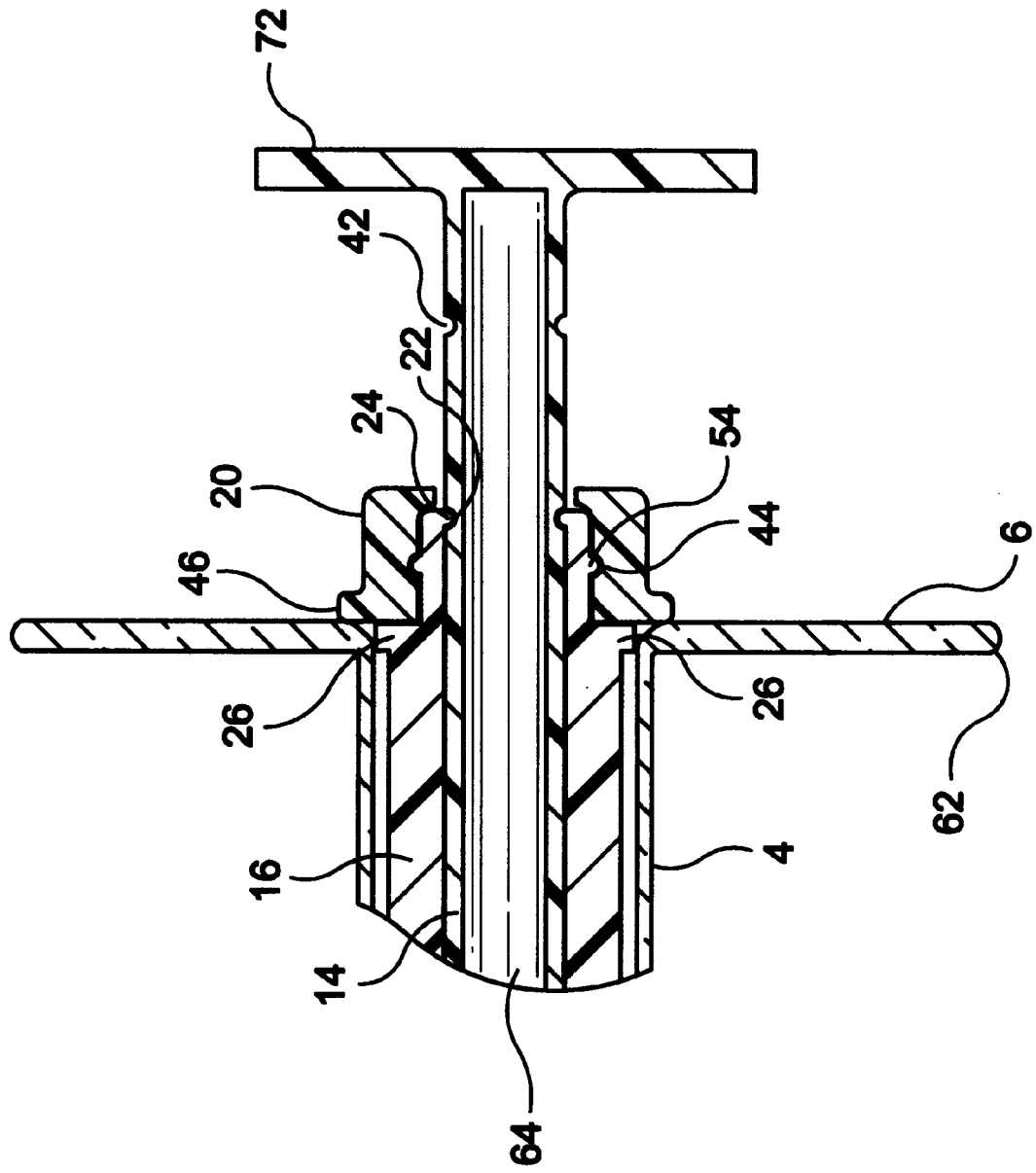
FIG. 8 is the view in FIG. 7 with the plunger rod assembly depressed and the retractable needle syringe inactivated.
Figure 9:
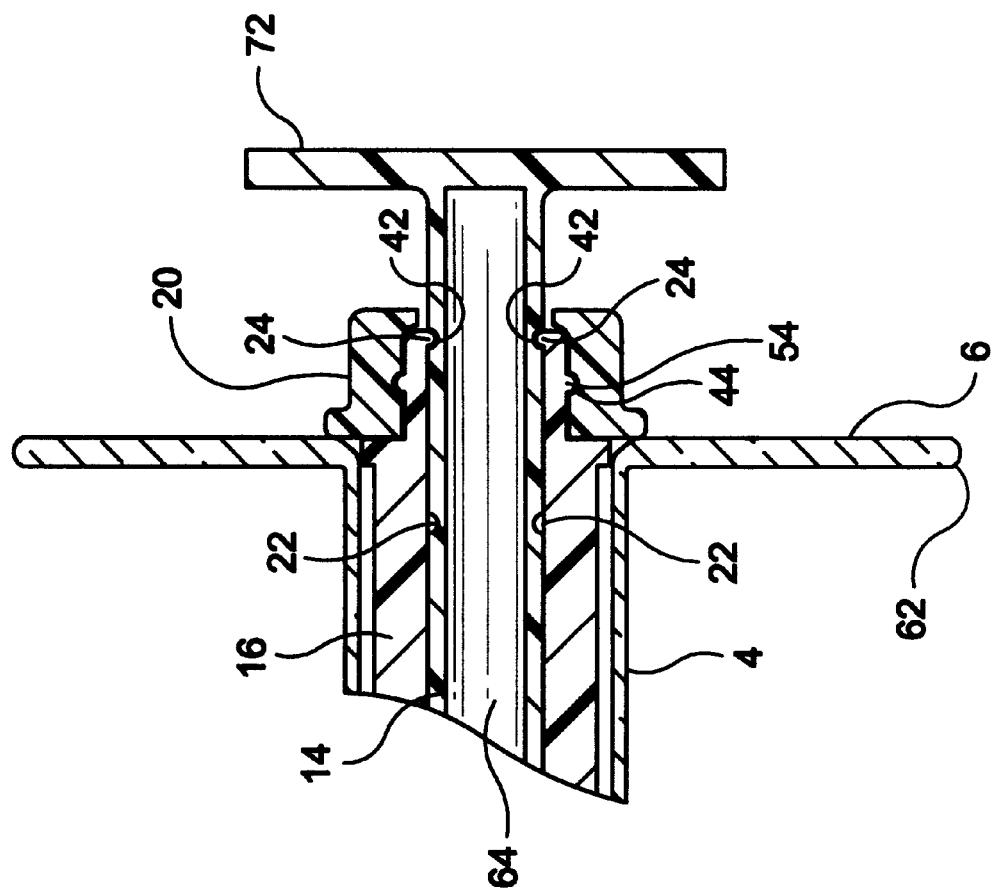
FIG. 9 is the view in FIG. 7 with the plunger rod assembly fully depressed and the retractable needle syringe activated by the inner rod.

Plunger assembly 12, as shown in FIG. 3, has a sealing member 34 attached to the outer member. Preferably, sealing member 34 is an elastomeric stopper. In addition, the outer member includes a plurality of supporting ribs 56 for imparting stiffness on the plunger rod assembly. Outer member 16 further includes a shoulder portion 26. The shoulder portion is for supporting the retaining ring. The outer member is attached to the retaining ring by a snap fit ring protrusion 54 on the outer member as shown in FIGS. 7–9. The ring is removable if sufficient force is applied. Protrusion 54 mates with a latching means 44 inside the retaining ring. Preferably, latching means 44 is a snap fit ring but it may be any type of latching means that can mate with protrusion 54 known to those skilled in the art. Such types of latching means include threads, detents, adhesives, and screws. Protrusion 54 is attached to latching means 44 so that the retaining ring can not be easily removed from the outer member. However, during the operative function of the plunger assembly, the ring can be disengaged from the outer member to allow the outer member to disengage from the inner member.

Inner member 14 is removably engaged in outer member 16. Inner member 14 includes at least one first detent 22 and the outer member includes at least one second detent 24 for removably fitting into the first detent. Retaining ring 20 is disposed on outer member 16 to restrict movement between the inner and the outer members by preventing the second detent from being displaced from the first detent. Preferably, the first detent is an annular groove on the inner member and the second detent is an inwardly directed protrusion. However, the first and second detents can be any type of removable fastener known to those skilled in the art. Such fasteners include, threads, snap fits, breakable adhesives, and frangible portions. When the second detent is displaced from the first detent, the inner member is free to slide within the outer member.

During depression of plunger assembly 12 into barrel 4, retaining ring 20 contacts proximal end 6 of barrel 4. Additional force to the inner member forces the inner member distally to disengage the inner member from the outer member. This movement allows the inner member to move within the outer member and activate the retractable needle syringe.

Figure 4:
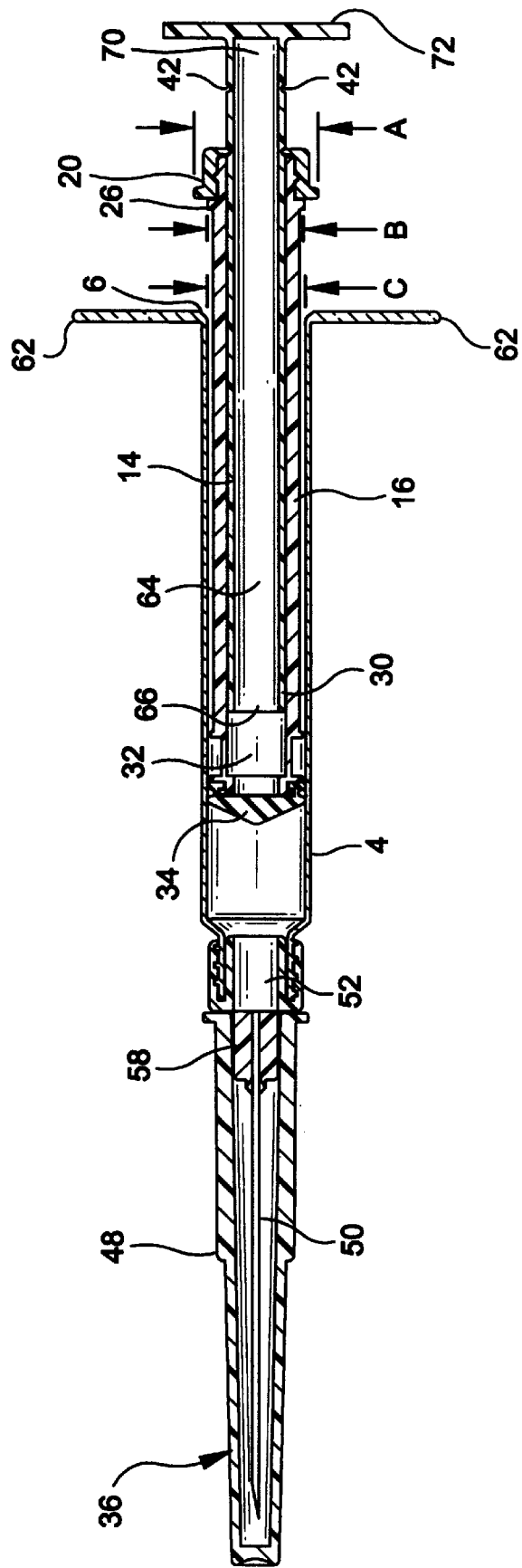
FIG. 4 is a cross-sectional view of FIG. 1 taken along lines 4—4.

Retractable needle syringe 2 is shown in FIG. 4 includes needle assembly 36, barrel 4 and plunger assembly 12. Needle assembly 36 further includes a needle 50 connected to a hub 58 and a retraction means 52 connected to the hub and the needle. Alternatively, the retraction means could include the hub, however, preferably the hub is a separate component from the retraction means. A shield 48 protects needle 50. Retraction means 52 when activated by plunger assembly 12 pulls needle 50 into inner member 14 through a conduit 64 formed within the inner member.

Retraction means 52 preferably is a spring-loaded activation system that withdraws needle 50 into inner member 14. However, retraction means 52 is not limited to such an embodiment and can be any type of retraction means that requires activation by the plunger assembly. Such alternative retraction means include but are not limited to retraction means that are attached to the plunger rod, retraction means that include elastomeric resilient members, and retraction means that include breakable hubs. The main advantage of the present invention is that the improved syringe plunger rod can be used with any retraction means that can be attached to the distal end of the syringe barrel.

Outer member 16 further includes shoulder portion 26 for supporting retaining ring 20. Retaining ring 20 further includes a lip portion 46. Lip portion 46 has a diameter "A" as shown in FIG. 4. Shoulder portion 26 has a diameter "B". Barrel 4 also has a inside diameter "C". The relationship between these diameters is such that diameter "B" is smaller than diameter "C" such that the outer member can slide easily within the barrel. Diameter "A" is larger than diameter "B" such that the retaining ring makes contact with the proximal end of the barrel instead of withdrawing inside the syringe barrel as does shoulder portion 26.

Outer member 16 further includes sealing member 34, which is preferably an elastomeric stopper. It is well known to those skilled in the art that sealing member 34 could be a sealing member other than elastomeric stopper. For example, such a sealing member may be a one-piece plunger rod, a natural rubber material, or a synthetic rubber material. Outer member 16 further includes snap fit ring 54. Ring 54 is preferably a snap fitting or press fitting as illustrated in FIGS. 7, 8 and 9. However, as previously described ring 54 can be any type of latch including threads, adhesives, heat welds or ultra sonic welding. Retaining ring 20 further includes latching means 44. Latching means 44 is preferably an annular groove. Latching means 44 retains retaining ring 20 onto outer member 16. Outer member 16 further includes at least one second detent 24 as shown in FIGS. 7–9. Preferably, second detent 24 is an inwardly directed protrusion. Detent 24 mates with first detent 22 of inner member 14.

Figure 5:
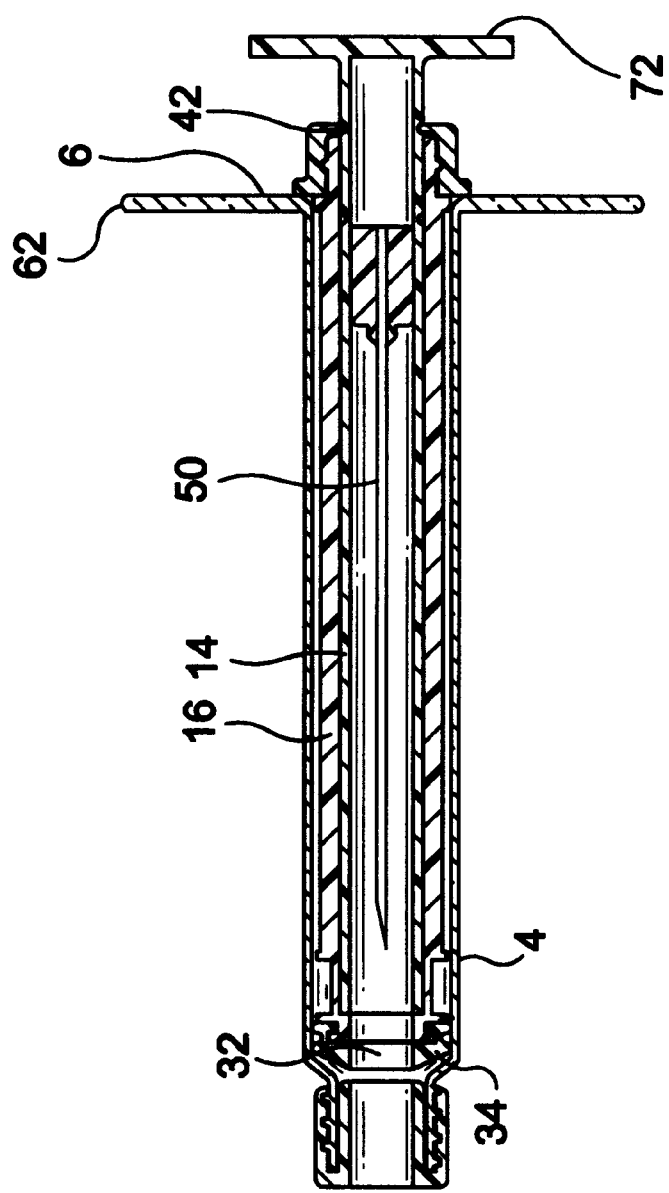
FIG. 5 is the view in FIG. 4 without the shield with the plunger rod assembly fully depressed and the needle retracted.

Inner member 14 includes at least one first detent 22, which mates with at least one-second detent 24. Preferably, at least one first detent 22 is an annular groove. Inner member 14 also includes a locking means 42. Preferably locking means 42 is also an annular groove. The locking means is for locking with at least one-second detent of the outer member when the plunger assembly or more specifically the inner member is fully depressed. This feature discourages re-use of the syringe since the detent of the outer member is permanently locked with the locking means of the inner member. Inner member 14 also includes a severing means 32. Severing member 32 is preferably a cutting ring as shown in FIGS. 4 and 5. Severing member 32 is capable of cutting through sealing member 34 to activate retraction means 52. FIG. 5 illustrates full retraction of needle 50 after the plunger assembly is fully depressed. It is the severing means that actually activates the retraction means to withdraw the needle when the inner member is fully depressed.

Severing means 32 is attached to the inner member by a fastening means 30. Means 30 is preferably a snap fit but it is within the scope of the invention that means 30 may include adhesives, insert molding, press fits, ultrasonic welding, heat welding, pins and screws. When the severing means penetrates sealing member 34, a hole 74 is formed as shown in FIG. 6. Hole 74 provides access to a conduit 64 so that when the needle is retracted by the retraction means the needle can enter the inner member by the conduit. Inner member 14 also includes a thumb depressor 72. Thumb depressor 72 is used to depress plunger assembly 12 into barrel 4.

Inner member 14 further includes conduit 64. Conduit 64 has an open end 66 and a closed end 70. The purpose of conduit 64 is to contain needle 50 when retraction means 52 is activated and retracts needle 50 into inner member of the plunger assembly.

The operation of the improved syringe plunger rod is relatively straightforward. Upon depressing the plunger assembly by thumb depressor 72 liquid is expelled out of needle 50. When shoulder portion 26 of outer member 16 is withdrawn into the proximal end of barrel 4, and lip portion 46 of retaining ring 20 comes in contact with proximal end 6 as shown in FIG. 8, further distally directed force on the thumb depressor will disengage the inner member from the outer member. Upon further distal force to thumb depressor 72, the inner member travels distally releasing first detent 22 from second detent 24. The retaining ring detaches from the outer member to allow the outer member to disengage from the inner member. As shown in FIG. 9 upon further distal motion of the inner member, second detent 24 of the outer member locks into locking means 42 of the inner member. This action disables the syringe and prevents re-use because the severing means at the distal end of the inner member is permanently locked through the sealing member creating hole 74 in the sealing member. Once inner member 14 has locking means 42 attached to second detent 24 of retaining ring 20, the plunger assembly is disabled and is no longer able to either aspirate or expel fluid. In addition, upon disengagement of the first detent from the second detent, the inner member is free to move within the outer member. This allows the severing means to cut through the sealing member and activate the retraction means.

Therefore, the retaining ring prevents premature activation. The retaining ring is attached to the outer member adjacent to the proximal end of the barrel. The ring prevents the spread of the inwardly directed protrusion of the outer member thereby keeping the protrusion inside the groove of the inner member. The ring also prevents relative motion between the inner and outer member to prevent the cutting ring to penetrate through the stopper. Not until the retaining ring is slid off of the inner and outer members can activation of the retractable needle syringe begin. During injection and expelling fluid stage, the ring travels with the plunger assembly until the fluid is almost fully expelled from the barrel. At that point, the proximal end of the barrel stops the ring. The ring slides off the outer member and the stopper bottoms in the barrel. Increased distal force to the inner member allows the protrusion of the outer member to slide out of the groove in the inner member and relative motion between both inner and outer members is allowed. The inner member and attached severing means advances through the stopper and through the retraction means. The retraction means is allowed to expand and retract the needle into the conduit of the inner member.

A separate embodiment could include on syringe barrel 4 at proximal end 6 an annular sleeve 40 as shown in FIG. 6. Annular sleeve 40 further dissuades one in attempting to withdraw the plunger assembly after fully depressed. The annular sleeve works by having the plunger assembly bottom out such that there is no surface area to grasp onto the plunger assembly. The retaining ring would function similarly as described above. In this embodiment, the ring would be dimensioned to fit within the annular sleeve and not the proximal end of the barrel so that the ring can still be activated through contact of the proximal end of the barrel.

In the embodiments depicted in FIGS. 1–9 are intended to be merely exemplary, and are not intended to depict all possible improved syringe plunger rods for retracting needle syringes. Rather, the improved syringe plunger rod can be used with any retracting needle syringe that has a removable hub assembly on the syringe barrel. The improved syringe plunger rod has the ability to prevent inadvertent activation of the retraction mechanism, which prematurely withdraws the needle.

What is claimed is:

1. A retractable needle syringe, comprising:

a barrel having a proximal end and a distal end; and a plunger assembly disposed in said barrel, said assembly having an inner member, an outer member, and a retaining ring, said inner member removably engaged in said outer member, said retaining ring disposed on said outer member to restrict movement between said inner and said outer members until said retaining ring contacts said proximal end of said barrel and said inner member is forced distally to disengage said inner member from said outer member which allows movement of said inner member within said outer member and activation of the retractable needle syringe.

2. The syringe of claim 1 wherein said inner member further includes at least one first detent, and said outer member further includes at least one second detent for removably fitting into said first detent.

3. The syringe of claim 2 wherein said outer member further includes a shoulder portion adjacent to said second detent for supporting said retaining ring.

4. The syringe of claim 2 wherein said first detent is an annular groove and said second detent is an inwardly directed protrusion.

5. The syringe of claim 1 wherein said retaining ring further includes a latching means for holding said ring on said outer member.

6. The syringe of claim 5 wherein said latching means is a snap fit ring.

7. The syringe of claim 1 wherein said inner tube further includes a severing member and said outer tube further includes a sealing member.

8. The syringe of claim 7 wherein said severing means is a cutter ring and said sealing member is an elastomeric stopper.

9. A retractable needle syringe, comprising:

a syringe barrel having a proximal end and a distal end; and a plunger assembly disposed in said barrel, said assembly having an inner member, an outer member, and a retaining ring, said inner member having at least one groove located adjacent to said proximal end and said outer member having at least one protrusion located adjacent to said proximal end for engaging in said groove, said retaining ring disposed on said outer member for locking said protrusion into said groove to restrict movement between said inner and said outer members until said retaining ring contacts said proximal end of said barrel and said inner member is forced distally to disengage said inner member from said outer member allowing movement of said inner member within said outer member and activation of the retractable needle syringe.

10. The syringe in claim 9 further including a needle assembly attached to said distal end of said syringe barrel.

11. The syringe in claim 9 wherein said syringe barrel further includes an annular sleeve mounted on said proximal end for preventing reuse of the syringe after said plunger assembly is depressed.

12. The syringe in claim 9 wherein said inner member further includes a locking means proximal to said groove for providing locking with said outer member and preventing reuse of said syringe.

13. The syringe in claim 9 wherein said retaining ring further includes a latching means for attachment to said outer member preventing removal of said retaining ring.

14. The syringe in claim 9 wherein said outer member further includes a shoulder portion adjacent to said protrusion for supporting said retaining ring, said shoulder portion sized smaller than said retaining ring to allow said retaining ring to contact said proximal end of said syringe barrel when said plunger assembly is depressed.

15. The syringe in claim 9 wherein said inner member further includes a severing means mounted adjacent to said distal end of said syringe barrel.

16. A retractable needle syringe comprising:

a syringe barrel having a proximal end and a distal end, said distal end having external threads;

a plunger assembly disposed in said barrel, said assembly having an inner member, an outer member, and a retaining ring, said inner member having a conduit with an open and closed end and at least one groove located adjacent to said proximal end, said outer member having at least one protrusion located adjacent to said proximal end for engaging in said groove, said retaining ring having a lip portion and disposed over said outer member for locking said protrusion into said groove to restrict movement between said inner and said outer members until said lip portion contacts said proximal end of said barrel and said inner member is forced distally to disengage said inner member from said outer member allowing movement of said members relative to each other; and a severing member attached to said inner member and adjacent to said distal end for allowing activation of the retractable needle syringe.

17. The syringe in claim 16 further including a needle assembly attached to said distal end of said barrel, said needle assembly having a needle and a retraction means for retracting said needle into said plunger assembly.

18. The syringe in claim 17 wherein said needle is retracted into said conduit of said inner member.

19. The syringe in claim 16 wherein said plunger assembly further includes a thumb depressor on said inner member adjacent to said closed end.

20. The syringe in claim 16 wherein said inner member further includes a fastening means for attaching said severing member to said inner member.

* * * * *